US006538105B1

(12) United States Patent
Drauz et al.

(10) Patent No.: US 6,538,105 B1
(45) Date of Patent: Mar. 25, 2003

(54) CATALYSTS FOR THE ENANTIOSELECTIVE EPOXIDATION OF C=C DOUBLE BONDS

(75) Inventors: Karlheinz Drauz, Freigericht-Somborn (DE); Stan M. Roberts, Neston (GB); Thomas Geller, Leverkusen (DE); Anupma Dhanda, Helsingoer (DK)

(73) Assignee: Degussa AG, Dusseldorf (DE)

( * ) Notice: Subject to any disclaimer, the term of this patent is extended or adjusted under 35 U.S.C. 154(b) by 0 days.

(21) Appl. No.: 09/453,711

(22) Filed: Dec. 3, 1999

(30) Foreign Application Priority Data

Dec. 3, 1998 (DE) .......................................... 198 55 859

(51) Int. Cl.[7] .............................................. C08G 69/02
(52) U.S. Cl. ..................... 530/324; 530/325; 530/326; 530/327; 549/523; 514/2; 514/12; 514/13; 514/14; 514/15
(58) Field of Search ................. 514/2, 12–15; 549/523; 530/324, 325, 326, 327

(56) References Cited

U.S. PATENT DOCUMENTS

| 3,846,399 | A | * | 11/1974 | Hirschmann | 260/112.5 |
|---|---|---|---|---|---|
| 4,525,495 | A | * | 6/1985 | Dorman | 523/205 |
| 4,525,576 | A | * | 6/1985 | Hayashi | 528/313 |
| 4,661,536 | A | * | 4/1987 | Dorman | 523/113 |
| 5,208,353 | A | * | 5/1993 | Flisak | 549/548 |
| 5,258,446 | A | * | 11/1993 | Enomoto | 524/538 |
| 5,486,598 | A | | 1/1996 | West et al. | 530/338 |

OTHER PUBLICATIONS

Itsuno et al., "Polymer–supported poly(amino acids) as new assymetric epoxidation catalyst of alpha, beta–unsaturated ketones", Journal of Organic Chemistry, vol. 55, 1990, p. 6047–6049.

Ebrahim et al., "Synthetic applications of polymeric alpha–amino acids", Tetrahedron: Asymmetry, NL, Elsevier Science Publishers, Amsterdam, vol. 8, No. 19, 1997, p. 3163–3173.

Banfi et al., "Asymmetric epoxidation of electron–poor olefins", Tetrahedron, vol. 40, No. 24, 1984, p. 5207–5211.

Oosterling et al., "End–grafting of (co)polyglutamates and (co)polyasparates onto Si–OH containing surfaces", Polymer, GB, Elsevier Science Publishers, vol. 36, No. 23, 1995, p. 4463–4470.

* cited by examiner

Primary Examiner—Christopher S. F. Low
Assistant Examiner—David Lukton
(74) Attorney, Agent, or Firm—Pillsbury Winthrop LLP

(57) ABSTRACT

Compositions are disclosed which comprise a homopolyamino acid and stereoisomers thereof adsorbed on an insoluble support material. The compositions are useful as catalysts for the stereoselective epoxidation of olefins.

11 Claims, No Drawings

CATALYSTS FOR THE ENANTIOSELECTIVE EPOXIDATION OF C=C DOUBLE BONDS

CROSS-REFERENCE TO RELATED APPLICATION

This application claims priority from German Application No. 198 55 859.7, filed on Dec. 3, 1998, the complete disclosure of which is hereby incorporated herein by reference.

BACKGROUND OF THE INVENTION

1. Field of the Invention

The present invention relates to novel supported, diastereomer-enriched and enantiomer-enriched homopolyamino acids, to a process for the production thereof, to the use thereof in a process for the enantioselective epoxidation of C=C double bonds and to preferred intermediates.

2. Background Information

Enantioselective epoxidation reactions are important reactions for the synthesis of chiral intermediates for organic synthesis. In particular, asymmetrical epoxidation of allyl alcohols according to Sharpless et al. and manganese-salen mediated enantioselective epoxidation according to Jacobsen et al. are well established in synthetic organic chemistry for the synthesis of chiral molecules (Sharpless et al., *J. Am. Chem. Soc.* 1980, 102, 5974; *J. Am. Chem. Soc.* 1987, 109, 5765; *J. Org. Chem.* 1986, 51, 1922; Jacobsen et al., *J. Am. Chem. Soc.* 1990, 112, 2801; *J. Am. Chem. Soc.* 1991, 113, 7063).

Another possibility for the asymmetric epoxidation of C=C double bonds has been discovered in the reaction of chalcones with hydrogen peroxide in the presence of enantiomer-enriched polyamino acids (Colonna et al., *Org. Synth.; Mod. Trends*, Proc. IUPAC Symp. 6th, 1986, 275; Julia et al., *Angew. Chem., Int. Ed. Engl.*, 1980, 19, 929).

The synthesis methods just stated all have the disadvantage that they are applicable to a relatively narrowly restricted range of substrates. On the basis of this fact and the continuing research activities in this area, it may be concluded that there is a need to discover further improved epoxidation processes.

To date, two different variants of the Julia/Colonna epoxidation reaction are known in the prior art, namely the two-phase and three-phase variants (S. M. Roberts et al. *Chem. Commun.* 1998, 1159; WO 96/33183). The two-phase variant makes use of an organic solvent and operates with oxidizing agents soluble in these solvents in the presence of the insoluble homopolyamino acids. The three-phase variant also makes use of water as the third phase in addition to the water-insoluble organic solvent. Water-soluble oxidizing agents may accordingly advantageously be used for the reaction, optionally in the presence of phase transfer catalysts.

However, it is clear from the last-stated publications relating to epoxidation reactions that the low space-time yields (reaction times of the order of days) and the sometimes poor ee values for many substrates are major deficiencies of these epoxidation methods with regard to their use in an industrial process.

On the other hand, it has been found that using immobilization techniques for enzyme mediated reactions may be advantageous with regard, for example, to the recoverability of the catalyst and raising the optical and chemical yield (EP 0 799 894 A2 and *Tetrahedron Asymmetry* 1991, 2, 931).

SUMMARY OF THE INVENTION

In the light of the prior art stated and discussed above, the object of the invention was accordingly to provide supported, diastereomer-enriched and enantiomer-enriched homopolyamino acids which allow the epoxidation of C=C double bonds in the presence of an oxidizing agent. In comparison with prior art supported catalysts, it was the intention that the novel compounds should in particular exhibit a higher rate of reaction combined with better chiral induction. Another object of the invention was to be able to produce the supported catalysts in the simplest and thus lowest cost manner possible and to ensure better handling characteristics with regard to recovery of the catalyst after the reaction, so resulting in advantages for use on an industrial scale.

These and further objects which are not stated in greater detail but may be derived in an obvious manner from the prior art are achieved by homopolyamino acids which are adsorbed on an insoluble support material. Preferably the homopolyamino acids have a chain length of 5 to 100 amino acids, more preferably 7 to 50. Homopolyamino acids from the group polyneopentylglycine, polyleucine, polyisoleucine, polyvaline, polyphenylalanine and polyalanine are preferred. In one preferred embodiment, the homopolyamino acids are crosslinked together or are enlarged by organic polymers. Preferred as support material for the homopolyamino acids are compounds containing silicon oxide, nitrocellulose, cellulose or activated carbon. The ratio of homopolyamino acid to support material is preferably between 1:7 and 2:1 parts by weight, more preferably between 1:1 and 1:4 parts by weight.

Because diastereomer-enriched and enantiomer-enriched homopolyamino acid is adsorbed on an insoluble support material, catalysts for enantioselective epoxidation are obtained which are extremely simple and thus low in cost to produce and furthermore, utterly surprisingly, are capable of considerably raising the rates of reaction in this reaction in comparison with prior art catalysts. Increased yield and enantiomer excesses in the epoxide products are simultaneously unexpectedly achieved. Furthermore, the supported homopolyamino acids according to the invention may be recycled very effectively and, by virtue of the enlargement and heterogenization thereof, such catalysts have very good handling characteristics on the industrial scale.

The supported catalysts may be produced using various diastereomer- and enantiomer-enriched homopolyamino acids. Preferably, however, homopolyamino acids from the group comprising polyneopentylglycine, polyleucine, polyisoleucine, polyvaline, polyalanine and polyphenylalanine are used. Of this group, polyneopentylglycine is the most highly preferred.

The chain length of the polyamino acids should be selected such that, on the one hand, chiral induction in the reaction is not impaired and, on the other, the costs for synthesizing the polyamino acids do not rise excessively. The chain length of the homopolyamino acids is preferably between 5 and 100, preferably 7 to 50, amino acids. A chain length of 10 to 40 amino acids is very particularly preferred.

A further preferred embodiment is that in which the homopolyamino acids are crosslinked with polyfunctional amines or are enlarged by other organic polymers. Crosslinking agents which are advantageously used are amines, such as for example 1,3-diaminopropane, 1st generation propyleneiminetetraamine dendrimers or crosslinked hydroxy- or aminopolystyrene. Polyethylene glycol/polystyrene based nucleophiles are preferably considered as polymer enlargers. Polyamino acids modified in this manner are described in *Chem. Commun.* 1998, 841 et seq., 1159 et seq. and *Tetrahedron Asymmetry* 1997, 8, pages 3165 et seq.

The insoluble support materials are those preferably synthesized on the basis of silicon oxide, such as for example molecular sieve, silica gel or zeolites together with Celite 521® or Celite Hyflo Super Cell®, Wessalith® Day P. Silica gels having defined pore sizes, such as for example CPC I or CPC II are also advantageous. Sugar derivatives such as nitrocellulose, cellulose or activated carbon are also preferred as support material.

The ratio of support material to polyamino acid is determined by two limits. On the one hand, only a certain quantity of polyamino acid may be adsorbed on the insoluble support, while on the other, chiral induction diminishes at a ratio of below 10 wt. % of polyamino acid to support. The ratio of homopolyamino acid to support material is preferably between 1:7 and 2:1 parts by weight, particularly preferably between 1:1 and 1:4 parts by weight.

The present invention also provides a simple but extremely advantageous process for the production of the homopolyamino acids, which is distinguished in that a mixture of homopolyamino acid and support material is suspended in an organic solvent and, after filtration, the residue is dried.

Another aspect of the present invention is the use of the supported homopolyamino acids in the process for the enantioselective epoxidation of C=C double bonds. The catalysts according to the invention are furthermore preferably used in a process which is performed in an apparatus which is capable of retaining only the catalyst. This apparatus preferably comprises an enzyme membrane reactor (C. Wandrey in Enzymes as Catalysts in Organic Synthesis, ed. M. Schneider, Dordrecht Riedel 1986, 263–284). Another preferred apparatus is a simple fixed bed reactor, such as for example a chromatography column.

A further aspect of the invention concerns polyneopentylglycine, which is preferably in a diastereomerically and enantiomerically pure form.

Providing polyneopentylglycine as a supported catalyst for the enantioselective epoxidation of substrates containing C=C double bonds unexpectedly makes it possible to achieve a substantial improvement in chiral induction during the epoxidation reaction in comparison with prior art homopolyamino acids (PLL has become established as the best catalyst for this reaction and is commercially available). It has moreover completely surprisingly been established that a more highly quantitative yield is obtained with a shorter reaction time.

Reference is made to the above-stated details relating to the homopolyamino acids with regard to chain length, crosslinking and polymer enlargement.

Polyneopentylglycine is preferably produced from the N-carboxylic anhydrides (NCAS) of neopentylglycine by nucleophilically initiated polymerization in an analogous manner to homopolyamino acids known in the prior art.

Polyneopentylglycine may be used in a process for the production of enantiomer-enriched epoxides. It is furthermore very particularly preferred to use homopolyneopentylglycine in a process for the production of supported epoxidation catalysts of the present invention.

As mentioned, the homopolyamino acids to be used in the epoxidation may be produced using prior art methods (c.f. for example Flisak et al., J. Org. Chem. 1993, 58, 6247). The method should be applied to both optical antipodes of the amino acids. Using a specific antipode of a polyamino acid correlates with the stereochemistry of the epoxide, i.e. a poly-L-amino acid gives rise to the optical antipode of the epoxide which is obtained with a poly-D-amino acid.

It has been found that treating the homopolyamino acid before the use thereof with a basic, aqueous medium, as described in EP 0 403 252 A2, brings about a further reduction in the rate of reaction in the epoxidation reaction.

Adsorption of the homopolyamino acid on the support material advantageously proceeds by 48 hours' stirring in an organic solvent, such as for example in ethers such as THF, in the presence of the support material. The solid material is then filtered out and dried.

In the present reaction according to the invention, the process is generally performed in that the homopolyamino acid or the modified derivatives, such as homopolyamino acid which has been crosslinked, polymer enlarged, or adsorbed on insoluble supports, is/are suspended in the reaction solvent mixture to be used, then the oxidizing agent is added, the pH value optionally adjusted and the substrate is added. The order of the process steps need not necessarily be followed, but the oxidizing agent should preferably be added to the mixture last, in order to avoid unintentional, uninduced epoxidation at the beginning of the reaction before addition of the catalyst, as this gives rise to lower ee values in the product. The processes are described in the prior art (S. M. Roberts et al., *Tetrahedron: Asymmetry* 1997, 8, 3163–3173, *J. Chem. Soc., Perkin Trans.* 1, 1996, 4, 343–348; *Chem. Commun.* 1998, 1159–1160 and literature cited therein; WO 96/33183; EP 0 403 252). The polyneopentylglycine or supported catalysts according to the present invention are used by simply replacing the polyamino acids used in the described processes with the novel catalyst. It should be noted that the catalysts according to the invention provide good results with both the two-phase and three-phase variants.

For the purposes of the invention, however, the two-phase variant is preferred for the supported homopolyamino acids.

The superiority of the supported catalysts over unsupported catalysts is illustrated by the following table 1.

TABLE 1

(see Example 1.a)

| No. | Support material | t [min] | Conversion [%] | ee value [%] |
|---|---|---|---|---|
| 1 | — | 120 | 43 | 93 |
| 2 | Silica gel | 30 | 99 | 95 |
| 3 | CPC I | 35 | 99 | 97 |
| 4 | CPC II | 30 | 76 | 95 |
| 5 | Molecular sieve | 120 | 93 | 95 |

The loading of the support material with homopolyamino acids has an influence on the quality of epoxidation (Table 2).

TABLE 2

(see Example 1.b)

Ph-CO-CH=CH-Ph → Ph-CO-epoxide-Ph

| No. | PLL/silica gel ratio | t [min] | Conversion [%] | ee value [%] |
|---|---|---|---|---|
| 1 | 1:1 | 30 | 97 | 94 |
| 2 | 1:3.4 | 30 | 99 | 95 |
| 3 | 1:7 | 210 | 72 | 93 |
| 4 | 1:10 | 210 | 47 | 93 |

Further Examples demonstrating the advantages of the supported homopolyamino acids are shown below (Table 3).

TABLE 3

(see Example 1.c)

R-CO-CH=CH-R' → R-CO-epoxide-R'

| No. | Cat. | t [h] | Conversion [%] | ee value [%] | R,R' |
|---|---|---|---|---|---|
| 1 | PLL | 24 | 50 | 93 | o-NH$_2$—Ph, Ph |
| 2 | PLL/support | 3 | 85 | 93 | o-NH$_2$—Ph, Ph |
| 3 | PLL | 26 | 56 | 89 | iPr, Ph |
| 4 | PLL/support | 14 | 78 | 93 | iPr, Ph |

The reaction mixtures are worked up using methods known to the person skilled in the art. The soluble epoxide is advantageously separated from the catalyst by filtration and then worked up in aqueous form. If desired, the epoxide may subsequently be purified chromatographically on silica gel.

The filterability of the supported catalysts is distinctly improved in comparison with unsupported catalysts. Homopolyamino acids assume the form of pastes, which clog the filter, whereas the supported counterparts are solids and may be separated with simple filtration apparatus.

This has positive effects primarily on reuse of the supported catalysts according to the invention. Catalyst losses on repeated use (the No. column indicates the number of uses) are substantially reduced in comparison with unsupported catalysts (Table 6).

TABLE 6

(see Example 1.d)

Ph-CO-CH=CH-Ph → Ph-CO-epoxide-Ph

| | | Supported PLL | | | Unsupported PLL | | | |
|---|---|---|---|---|---|---|---|---|
| No. | t [min] | Yield [%] | ee [%] | Cat. loss [%] | t [min] | Yield [%] | ee [%] | Cat. loss [%] |
| 1 | | | | | | | | |
| 2 | 200 | 96 | 93 | 3 | 60 | 48 | 97 | 10 |
| 3 | 115 | 90 | 95 | 3 | 60 | 82 | 97 | 7 |
| 4 | 95 | 94 | 95 | 7 | 60 | 81 | 98 | 8 |
| 5 | 105 | 97 | 98 | 2 | 60 | 79 | 97 | 4 |

TABLE 6-continued (see Example 1.d)

Ph-CO-CH=CH-Ph → Ph-CO-epoxide-Ph

| | | Supported PLL | | | Unsupported PLL | | | |
|---|---|---|---|---|---|---|---|---|
| No. | t [min] | Yield [%] | ee [%] | Cat. loss [%] | t [min] | Yield [%] | ee [%] | Cat. loss [%] |
| 6 | 100 | 91 | 95 | 1 | 150 | 82 | 97 | 8 |
| 7 | 110 | 95 | 98 | 2 | >240 | 80 | 96 | 15 |

The above results demonstrate the advantage of using the homopolyamino acids in supported form over using them in unsupported form with regard to activity, selectivity, handling and recyclability. This is achieved solely by simply adsorbing the homopolyamino acids on insoluble support materials, which seems extremely surprising yet consequently all the more advantageous.

Results of the epoxidation reactions of PLL-CLAMPS are compared below with those for PLN-CLAMPS. PLL means poly-L-leucine, PLN means poly-L-neopentylglycine. All results were measured by chiral HPLC (see Example 2).

TABLE 7

| Conditions | Time [h] | Conversion [%] | ee value [%] |
|---|---|---|---|
| 2-phase/PLL | 18 | 90 | 95 |
| 2-phase/PLN | 6 | 98–100 | >95 |
| 3-phase/PLL | 0.5 | 90 | 95 |
| 3-phase/PLN | 0.5 | 90 | 96 |

TABLE 8

| Conditions | Time [h] | Conversion [%] | ee value [%] |
|---|---|---|---|
| 2-phase/PLL | 22 | 95 | 94 |
| 2-phase/PLN | 3 | 90 | 98 |

TABLE 9

| Conditions | Time [h] | Conversion [%] | ee value [%] |
|---|---|---|---|
| 2-phase/PLL | 8 | 83 | 95 |
| 2-phase/PLN | 2 | 93 | >95 |

TABLE 10

| Conditions | Time [h] | Conversion [%] | ee value [%] |
|---|---|---|---|
| 2-phase/PLL | 32 | 60 | 60 |
| 2-phase/PLN | 7 | 80 | 75 |

As is clearly evident from these examples, poly-L-neopentylglycine also has distinct advantages over known prior art homopolyamino acids with regard to activity and selectivity.

Using the homopolyamino acids and modified derivatives presented here thus, on the one hand, gives rise to better ee values on epoxidation and, on the other, distinctly reduces reaction times for this transformation. This could not straightforwardly be derived from the prior art. While, as stated above, it is indeed known to absorb enzymes on insoluble supports, it is not consequently in the least obvious that the compounds according to the invention will be improved by such a measure. On the contrary, the person skilled in the art could have expected that adsorption of the polymer on the solid support material would bring about a conformational reorientation and immobilize this conformation such that the chiral induction thereof would consequently be impaired. Since the mechanism of the stated epoxidation reaction is not yet known, it was extremely surprising that the described immobilization should bring about an increase in activity and induction and not the opposite.

Moreover, the possibility of binding enzymes to insoluble supports does not make it in the least obvious that the homopolyamino acids at issue in the present case may be similarly firmly adsorbed on the insoluble support materials. Enzymes are macromolecules, which, in comparison with the homopolyamino acids of the present invention, may enter into quite different non-covalent interactions with substrates.

In comparison with the chemically modified, polymer enlarged homopolyamino acids, the production of the supported homopolyamino acids by physical adsorption is so straightforward and thus low in cost that the use thereof is preferred on the industrial scale. It is furthermore advantageous that the handling properties and recoverability are distinctly improved in comparison with unsupported homopolyamino acids, as the heterogenization results in better filterability. Standard prior art homopolyamino acids are pasty and capable of clogging the pores of filters and membranes, which would cause considerable difficulties, especially for the industrial use thereof. The epoxidation catalysts according to the invention are accordingly ideally suitable for industrial use in advantageous apparatus such as the fixed bed reactor and enzyme membrane reactor (C. Wandrey in Enzymes as Catalysts in Organic Synthesis, ed. M. Schneider, Dordrecht Riedel 1986, 263–284), which permit continuous or semi-continuous performance of the reaction, which is highly preferred for an industrial process.

This invention accordingly for the first time makes the use of the catalysts according to the invention in an industrial process appear economically advantageous.

The person skilled in the art takes the term homopolyamino acids to mean polymers of amino acids from a single source. For the purposes of the invention, however, the homopolyamino acids used may also comprise copolymers of various amino acids, which, however, have domains determining chiral induction which should consist of uniform amino acids. The term homopolyamino acids accordingly also refers to polymers synthesized from heterochiral amino acids. It is again the case that the domains which determine chiral induction should consist of a stereochemically uniform sequence of amino acids.

Supported is taken to mean the physical adsorption of molecules on the support materials according to the invention.

For the purposes of the invention, the term enantiomer-enriched should be taken to mean the mixture of an enantiomer with the optical antipode thereof in a proportion ranging between >50% and <100%.

For the purposes of the invention, the term diastereomer-enriched is taken to mean the mixture of an diastereomer with the other diastereomer thereof in a proportion ranging between >50% and <100%.

DETAILED DESCRIPTION OF THE INVENTION

EXAMPLES

1) Use of Supported PLL as Catalyst

Standard conditions for catalyst testing (apply to all supported catalysts, unless otherwise stated).

Catalyst production: 70 mg of PLL (1,3-diaminopropane used as polymerization initiator, Chem. Commun. 1998, 1159; S. M. Roberts et al. J. Chem. Soc. Perkin Trans. I, 1998, 3171) are stirred with 240 mg of support material in 2 ml of THF for 48 h using a magnetic stirrer. The suspension is then filtered and the residue dried at 1.1 kPa and RT for 1 h, then at 50–55° C. and 0.008 kPa for 7 h.

Epoxidation reaction: 18 mg of trans-chalcone, 10 mg of UHP (urea peroxide compound), 155 mg of supported catalyst and 15 µl of DBU are stirred in 1 ml of THF at RT. Conversion and ee value are determined by chiral HPLC.

HPLC conditions: Chiral HPLC was performed using Chiralpak AD columns. To this end, an aliquot of the reaction mixture was taken and, once filtered, analysed at 254 nm at a flow rate of 1.00 ml/min with 10 wt. % EtOH/hexane as mobile solvent.

1.a) Various Supports

Silica gel=Silica gel 60 (230–400 mesh, Merck)
CPC I=controlled pore size carrier (375 Å, 30–45 mesh, Fluka)
CPC II=controlled pore size carrier, silane coated, derived from the 3-aminopropyl residue (375 Å, 30–45 mesh, Fluka),
Celithe 521® (Aldrich), Celithe Hyflo Super Cell® (Fluka), Wessalith® Day P.=$SiO_2$,
Molecular sieve ($SiO_2$, batch: MPM TI, Degussa)
Zeolite TS1 (5.5 Å, 3% Ti).
Reaction Conditions for PLL Use:
Similar to literature methods—two-phase variant.
Conversions and ee values were determined by chiral HPLC.
Retention times of the enantiomeric epoxides: 15.9 min (main enantiomer) and 23.7 min.
In entry 1, support materials and homopolyamino acid were combined only just before epoxidation.

1.b) Differing Loading

Supported catalysts with the corresponding polyamino acid/support ratios were otherwise produced in accordance with the standard process. Silica gel was used as the support material.
Conversion and ee value were detected by chiral HPLC. Retention times, see Example 1.a).

1.c) Variation in Substrates

Support material: silica gel; ratio 1:3.4
Reaction conditions for PLL comparison:
Similar to literature methods—two-phase variant.
Entries 1 and 2:
Conversion and ee value were detected by chiral HPLC, 14% EtOH in hexane, 230 nm.
Retention times of the enantiomeric epoxides: 25.6 min (main enantiomer) and 31.2 min.
Entries 3 and 4:
Conversion and ee value were detected by chiral HPLC, 5% EtOH in hexane, 230 nm, flow rate 0.7 ml/min.
Retention times of the enantiomeric epoxides: 12.6 min (main enantiomer) and 23.3 min.

1.d) Catalyst Recycling

Reaction conditions for PLL comparison: Similar to literature methods—two-phase variant (initial quantity of catalyst 2.0 g).
Catalyst Recovery:
After the reaction, the mixture was filtered, the filter residue washed with water/acetone (1:1), acetone and EtOAc and then dried under an oil pump vacuum.
Reaction conditions for use of the supported catalyst:
Support material: silica gel; ratio 1:3.4
116 mg of trans-chalcone, 65 mg of UHP, 100 μl of DBU were reacted in 6.5 ml of THF at RT with the appropriate quantity of supported catalyst (initial quantity 1.0 g).
Catalyst Recovery:
After the reaction, the mixture was filtered, the filter residue washed with THF, EtOH and, finally, again with THF. The residue was then dried under the standard conditions.

2) Use of Polyneopentylglycine (PLN) as Catalyst

Chiral HPLC was performed using Chiralpak AD columns. To this end, an aliquot of the reaction mixture was taken and, once filtered, analysed at a flow rate of 1.00 ml/min.

Testing of the substrates revealed the following results:

| Substrate | Mobile phase | $R_t$ [min] of the enantiomeric epoxides | λ [nm] |
|---|---|---|---|
| 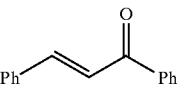 | 10% EtOH in hexane | 14.0 and 20.5 | 254 |
| 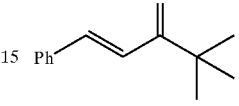 | 1% i-PrOH in hexane | 15.0 and 22.0 | 230 |
| 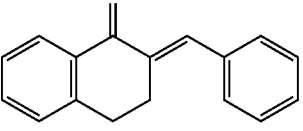 | 1% i-PrOH in hexane | 14.0 and 21.5 | 230 |
| 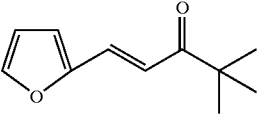 | 10% EtOH in hexane | 17.3 and 21.1 | 230 |

Production of Catalyst (PLN-CLAMPS):

A dried 2 l, three-necked flask is filled with 0.1400 mol of neopentylglycine (commercially available) and kept at 100° C. for 24 h under a vacuum. The flask is then purged with nitrogen and the contents combined with 1 l of dry THF. Once the suspension has been heated to approx. 50° C., 0.0513 mol of triphosgene is added dropwise over a period of 15 minutes. After 2 h, the solution is cooled to RT, filtered and evaporated under a vacuum. The crystalline residue is dissolved in a minimum quantity of THF and precipitated by addition of 1 l of n-hexane. The NCA of L-neopentylglycine is obtained in 85% yield as a colourless solid of melting point 129.3–131.2° C.; $\delta_H$ (300 MHz; $CDCl_3$) 1.02(9H, s, 3×$CH_3$), 1.65 (1H, dd, J 14.7 and 9.9, β-$CH_2$), 2.0 (1H, dd, J 14.7 and 2.4, β-$CH_2$), 4.38 (1H, dd, J 9.9 and 2.4, α-CH), 6.8 (1H, br, NH).

0.1180 mol of L-neopentylglycine NCA is combined in 250 ml of THF with (3.668 mol) of CLAMPS (crosslinked aminopolystyrene) and the mixture was stirred 5 days under nitrogen at RT. The suspension is then filtered and the filtrate is treated with water for 30 min, then with acetone/water (1:1), acetone/water (4:1), acetone (2×), EE (2×), diethyl ether (2×) and then dried under a vacuum.

The polymer is then activated for several hours in a mixture of toluene/4 M sodium hydroxide solution (2.5:1).

PLL-CLAMPS may be produced in an analogous manner (c.f. also Chem. Commun. 1998, 1159).

Epoxidation:

3-phase variant 100 mg of the polymer (PLL-CLAMPS or PLN-CLAMPS) in 0.8 ml of toluene and 0.2 ml of 4 M NaOH (12 eq.) are combined at 0° C. in an ice bath with 0.2 ml of 30% aqueous $H_2O_2$ (21 eq.) and kept at this temperature for 6 h. The enone (1 eq.), a further 0.5 ml of $H_2O_2$ and 0.2 ml of toluene are added to the mixture. Samples are taken after various periods of time and analysed by chiral HPLC.

2-phase variant 100 mg of the polymer (PLL-CLAMPS or PLN-CLAMPS) and 0.24 mmol of the enone in 0.8 ml of THF are combined with 0.36 mmol (1.5 eq.) of DBU and 0.28 mmol of UHP (urea hydrogen peroxide compound). The mixture is stirred at RT. Samples are taken after various periods of time and analysed by chiral HPLC.

Publications cited herein are hereby incorporated by reference in their entirety.

What is claimed is:

1. A composition comprising a mixture of a first optical isomer of polyneopentylglycine, the enantiomer of said first optical isomer, and a diastereomer of said first optical isomer, wherein the amount of said first optical isomer exceeds the amount of said enantiomer of said first optical isomer and the amount of diastereomer of said first optical isomer, but is less than 100% of the total weight of polyneopentylglycine in said mixture.

2. The composition of claim 1, wherein said first optical isomer of polyneopentylglycine has a chain length of 5 to 100 amino acids.

3. The composition of claim 2, wherein said first optical isomer of polyneopentylglycine has a chain length of 7 to 50 amino acids.

4. A process for the production of a supported epoxidation catalyst comprising adsorbing onto an insoluble support material the composition of claim 1, and then isolating said supported catalyst.

5. The process of claim 4, wherein said composition comprises a mixture of a first optical isomer of polyneopentylglycine, the enantiomer of said first optical isomer, and a diastereomer of said first optical isomer, wherein the amount of said first optical isomer exceeds the amount of said enantiomer of said first optical isomer and diastereomer of said first optical isomer, but is less than 100% of the total weight of polyneopentylglycine in said mixture.

6. A composition comprising a mixture of a first optical isomer of polyneopentylglycine, the enantiomer of said first optical isomer, and a diastereomer of said first optical isomer, wherein:

(a) said first optical isomer of polyneopentylglycine is in a form crosslinked by means of polyfunctional compounds; and (b) the amount of said first optical isomer exceeds the amount of said enantiomer of said first optical isomer and said diastereomer of said first optical isomer, but is less than 100% of the total weight of polyneopentylglycine in said mixture.

7. A composition comprising a mixture of a first optical isomer of polyneopentylglycine having a chain length of 5 to 100 amino acids, the enantiomer of said first optical isomer and a diastereomer of said first optical isomer, wherein the amount of said first optical isomer exceeds the amount of said enantiomer of said first optical isomer and the amount of the diasteromer of said first optical isomer but is less that 100% of the total weight of polyneopentylglycine in said mixture, and wherein said mixture is adsorbed onto an insoluble support material.

8. A composition comprising a mixture of a first optical isomer of polyneopentylglycine having a chain length of 5 to 100 amino acids, the enantiomer of said first optical isomer and a diastereomer of said first optical isomer, wherein the amount of said first optical isomer exceeds the amount of said enantiomer of said first optical isomer and the amount of the diasteromer of said first optical isomer but is less that 100% of the total weight of polyneopentylglycine in said mixture, and wherein said polyneopentylglycine is enlarged with organic polymers.

9. A process for preparing polyneopentylglycine comprising:

(a) reacting molecules of neopentylglycine N-carboxyanhydride by nucleo-philically initiated polymerization, said reaction proceeding for a time and under conditions effective to produce polyneopentylglycine; and (b) recovering said polyneopentylglycine.

10. A process for preparing an optically active epoxide, comprising:

(a) reacting an olefin-containing compound with an oxidizing agent in the presence of polyneopentylglycine adsorbed on an insoluble support material, for a time and under conditions effective to convert the olefin to said optically active epoxide; and (b) recovering said optically active epoxide.

11. The process of claim 10, wherein both said olefin-containing compound and said epoxide are enriched in a single enantiomer.

* * * * *